United States Patent [19]
Goodman et al.

[11] Patent Number: 4,883,659
[45] Date of Patent: Nov. 28, 1989

[54] SKIN TREATMENT PREPARATION

[75] Inventors: Jack J. Goodman, Morristown, N.J.;
Harvey S. Tauman, Boca Raton, Fla.;
Charles Fox, Fairlawn; Thomas J.
Hart, Dover, both of N.J.

[73] Assignee: Dento-Med Industries, Inc., Boca Raton, Fla.

[21] Appl. No.: 235,630

[22] Filed: Aug. 24, 1988

[51] Int. Cl.$^4$ .................. A61K 31/74; A61K 31/78; A61K 7/00; C08F 18/00
[52] U.S. Cl. .......................... 424/78; 424/81; 424/70; 514/937; 514/938; 514/943; 514/844; 526/320; 524/322
[58] Field of Search .................... 526/320; 424/78, 81, 424/70; 514/937, 938, 943, 844, 845; 524/322

[56] References Cited
U.S. PATENT DOCUMENTS 3,577,518  5/1971  Shepherd et a. ................. 424/81
4,424,234  1/1984  Alderson et al. ............ 424/DIG. 5

FOREIGN PATENT DOCUMENTS 2144133  2/1985  United Kingdom ............... 514/844

*Primary Examiner*—Joseph L. Schofer
*Assistant Examiner*—Carmen B. Pili-Curtis
*Attorney, Agent, or Firm*—George A. Skoler

[57] ABSTRACT

A water resistant, non-gummy hygroscopic, flexible and pliable thin film of 2-hydroxyethyl methacrylate homopolymer deposited on an epidermal surface, a stable emulsion from which the film can be made and a special process for the manufacture of the stable emulsion, utilizing an ammonium salt of a long chain fatty acid as an emulsifying agent therein. The topical application of stable emulsions utilizing an ammonium salt of a long chain fatty acid as an emulsifying agent therein, from which a water resistant, non-gummy, hygoscopic, flexible and pliable thin film of 2-hydroxyethyl methacrylate homopolymer is deposited on an epidermal surface. Special solvent combinations and emulsification techniques are described.

9 Claims, No Drawings

SKIN TREATMENT PREPARATION

Related Applications

This application is related to copending applications Ser. No. 07/235,601 pending and Ser. No. 07/236,053 pending, both filed on even date herewith.

BRIEF DESCRIPTION OF THE INVENTION

A water resistant, non-gummy, hygroscopic, flexible and pliable thin film of 2-hydroxyethyl methacrylate homopolymer deposited on an epidermal surface, a stable emulsion from which the film can be made and a special process for the manufacture of the stable emulsion. The topical application of stable emulsions from which a water resistant, non-gummy, hygroscopic, flexible and pliable thin film of 2hydroxyethyl methacrylate homopolymer is deposited on an epidermal surface.

BACKGROUND TO THE INVENTION

Charles Fox, Cosmetics and Toiletries, Vol. 99, pages 41-54, March 1984, made the comment that "almost any cosmetic can be formulated as a cream or lotion."

Fox points out that skin moisturizing properties which enhance smoothness, suppleness and softness of the skin represent a primary property of cosmetic creams and lotions. There is a vast and diverse array of oils, moisturizers and emollients which are employed for this purpose, such as mineral oil, propylene glycol and silicones. Many materials are employed because they introduce diverse properties to the cosmetic formulation. Fatty alcohols serve as moisturizing agents and also provide emulsion stability viscosity control and consistency. One attribute that fatty alcohols are noted to provide is a "smooth finish on rubout" (See Fox supra page 52). Fox notes that stearic acid is a moisturizer and it is used also to form a soap emulsion system. Fox demonstrates the wide array of components which one may introduce to a cosmetic lotion.

Almost all cosmetics will provide a degree of protection to the skin to which it is applied. The level of protection is dependent upon a number of factors:

1. The uniformity of the cosmetic as a film on the epidermal surface;
2. The resistance of the film to attack by body liquids and perspiration;
3. The volatility of the cosmetic;
4. The resistance of the film to abrasive and frictional attack; and
5. The resistance of the film to ultraviolet light.

A number of polymeric thermoplastic materials have been utilized for a variety of cosmetic applications. Many of these materials are water soluble or dispersible. Consequently, any lotion in which they are provided will typically lack in moisture resistance. Even though polymeric thermoplastics are large molecules, i.e., macromolecules, solubilization of a film containing these large molecules by moisture can remove them as rapidly from the treated surface as would a comparable cosmetic formulation made from lower molecular weight materials. This stems from the fact than the macromolecule is typically present in small quantities in the cosmetic resulting in a small quantity of the macromolecule deposited on the skin. The erosion of the macromolecule by the relatively large mass of moisture is sufficient to quickly wipe away the presence of the macromolecule from the skin surface.

It would be desirable to utilize macromolecules which are moisture resistant in cosmetic preparations because they could provide a level of cosmetic permanency on the epidermal surface. R. S. Berger, et al., J. Soc. Cosmet. Chem., 29, pp. 641-649 (1078) describe the use of sunscreen agents such as octyl p-N,N-dimethylamino benzoate (PABA) and an ammonium acrylate/acrylate ester polymer (see the "Synopsis"). The authors state "An acrylate film-forming polymer was selected as the primary film-former for the sunscreen preparation. This polymer is skin-adherent and water-resistant. When dried on the skin, however, the film is easily removed with soap and water. An oil-in-water emulsion containing the acrylate polymer and octyl dimethyl PABA was prepared. Ammonium isostearate served as the primary emulsifier." (see page 642)

"An acrylate film-forming polymer was selected with could be solubilized by forming the ammoniated salt in an anionic soap emulsion. When the sunscreen preparation dries on the skin, the ammonia evaporates, fixing the insoluble polymer to the skin. Due to this 'fugitive amine' transformation, the film is insoluble in water and resistant to rub-off. It is easily removed, however, by washing with soap and water . . . " (see page 646)

However, the use of moisture resistant macromolecules in general is quite difficult in this application. Frequently, such moisture resistent macromolecules have poor film forming properties when deposited as an extremely thin film on an epidermal surface and should they possess good or adequate film forming properties, they frequently lack the essential properties of a suitable cosmetic.

This can be appreciated by recognizing that in a typical oil in water cosmetic formulation in which the macromolecule is present as a minor quantity, it is difficult to formulate the macromolecule in such a way that it can be released from the emulsion of application as a uniform, easily applied film containing whatever plasticization required for the cosmetic application. For example, the plasticization aids may separate from the macromolecule on application because the emulsion is being broken by an alteration of the chemistry of the emulsion. In addition, there are a number of important properties required of such a macromolecular layer on skin. For example, it is typically necessary for a film to be sufficiently thin enough in epidermis treatment that the recipient does have adverse sensations resulting therefrom. The film should not be greasy, brittle, tacky, gummy or oily. The film should not be receptive to inks, dyes, oils or other materials to which the surface treated skin is in contact. For example, one would not wish to have a cosmetic treatment which dissolves news print, or itself be dissolved by sebaceous oils. Because macromolecules have the capacity of engendering high viscosities, their utilization should provide pore penetrability sufficient to achieve effective bonding to the skin yet provide a film possessed of moisture permeability.

The attributes required of an effective cosmetic material which possess moisture resistant properties on an epidermal layer are difficult to achieve. The conversion of an effective moisture resistant thermoplastic film forming macromolecule into an effective cosmetic material requires
1. the ability to deposit the film from a stable liquid phase;
2. the deposition of a uniform plasticized film on the surface of the skin which possesses
   i. good tactility and flexibility;
      a. therefore free of greasiness, brittleness, tackiness, gumminess and oiliness;
   ii. resistance to inks, dyes, oils or other materials to which the surface treated skin is in contact or is generated by the body, such as sebaceous oils;
   iii. ready penetrability into the skins pores and velvety smooth skin feel ;
   iv. non-gummy rubout characteristics; and
   v. moisture resistance combined with air and moisture permeability (breathability).

Hydroxyethyl methacrylate homopolymer [poly(2-hydroxyethyl methacrylate)], referred to herein by the abbreviation "PHEMA," is a macromolecule[1] which, broadly speaking, has the repeating unit formula

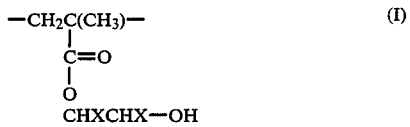

wherein each X is hydrogen or methyl and not more than one X is methyl. The most common characterization of PHEMA possesses X as hydrogen only.

1. "Macromolecule," as used herein, embraces a polymeric structure composed of repeating mer units. A polymer is defined herein as a macromolecule larger than an oligomer, the latter being defined as a structure of up to about 15 repeating mer units.

Hydroxyethyl methacrylate homopolymer and copolymers have been described in a variety of patents for use in cosmetic applications. For example, Shepherd et al., U.S. Pat. No. 3,574,822, patented Apr. 13, 1971,[2] describe the use of powdered PHEMA or solutions of PHEMA for a number of applications such as hair setting composition, flavoring release component, cosmetic emulsions, insect repellent, sunscreen lotion, aerosols, nail enamels, cleansing cream, vanishing foundation cream, hand cream, emollient cream, face powder, baby powder, and lipstick. This patent shows that PHEMA is normally a brittle material and sufficiently brittle that it can be used to set hair and act as a lacquer for nail covering. Example 17 of the patent addresses the plasticization of PHEMA by incorporating glycerol, sorbitol, diethylene glycol, dipropylene glycol, ethylene glycol, and/or propylene glycol as plasticizers . This resulted in a more flexible hair spray but even with such plasticization the polymer was stiff enough to hold the hair in tension. This demonstrated that such a polymer, applied to the skin, would cause an adverse sensation to the user reflected by the fact that the film on the skin would resist a skin mobility.

2. Note the following related patents to Shepherd, et al.: U.S. Pat. Nos. 3,577,518; 3,681,089; 3,681,248; 3,697,643; and 3,914,405.

Abrahams, U.S. Pat. No. 3,963,685, Patented June 15, 1976, describes a process for making PHEMA. The patent talks in terms of a number of uses for PHEMA including those set forth in the aforementioned Shepherd, et al. patents.

THE INVENTION

This invention relates to the formation of a water resistant, non-gummy, hygroscopic, flexible and pliable thin layer of PHEMA film deposited from an oil and water emulsion utilizing an ammonium salt of a long chain fatty acid as an emulsifying agent therein, on an epidermal surface, and insolubilized therefrom by the decomposition of the ammonium salt. It also relates to a stable emulsion of a PHEMA, and as well, to a special process for the manufacture of the stable cosmetic emulsion, utilizing an ammonium salt of a long chain fatty acid as an emulsifying agent therefor. The invention embraces the topical application of stable emulsions from which a water resistant, non-gummy, hygroscopic, flexible and pliable thin film of PHEMA is deposited on an epidermal surface to provide cosmetic attributes from an oil and water emulsion utilizing an ammonium salt of a long chain fatty acid as an emulsifying agent therein.

The invention contemplates the formation of a water resistant, non-gummy, hygroscopic, flexible and pliable thin layer of PHEMA film as part of a cosmetic deposited deposited from an oil and water emulsion utilizing an ammonium salt of a long chain fatty acid as an emulsifying agent therein, on an epidermal surface, and insolubilized therefrom by the decomposition of the ammonium salt. It also relates to a cosmetic formulation of a stable emulsion of a PHEMA, and as well, to a special process for the manufacture of the stable emulsion, utilizing an ammonium salt of a long chain fatty acid as an emulsifying agent therefor. The invention embraces the topical application of a cosmetic formulation of a stable emulsions from which a water resistant, non-gummy, hygroscopic, flexible and pliable thin film of PHEMA is deposited on an epidermal surface utilizing an ammonium salt of a long chain fatty acid as an emulsifying agent therein.

The invention relates to a water resistant, thin layer PHEMA containing a plurality of plasticizers each having a different solvency power for PHEMA, thereby controlling the pliability of the layer of PHEMA and being rendered part of a water resistant layer of PHEMA by the decomposition of the emulsifying agent of an emulsion in which the PHEMA and the plural plasticizers are formulated. The invention relates to a cosmetic oil in water emulsion containing an oil phase and a water phase and containing in the water phase, PHEMA and at least three solvents for PHEMA plus an ammonium salt of a fatty acid as an emulsifying agent therefor. The solvents for PHEMA comprise
   i. an active and volatile solvent,
   ii. a lesser intermediately active and nonvolatile solvent and
   iii. at least active and nonvolatile solvent.

The invention embraces the formation of an oil in water emulsion made in a multi-stepped sequence involving
1. the separate formation of oil and water phases,
2. combining the oil phase with a water phase into either an oil in water emulsion or into a water in oil emulsion,
3. providing PHEMA in solution in combination with a plasticizer therefor,
4. providing the solution in an aqueous phase,
5. providing part of an emulsifying agent in the desired oil in water emulsion as part of an aqueous phase and part in the oil phase, and forming the emulsifying agent upon combining the various phases of the oil in water emulsion, and
6. combining the various phases to make the oil in water emulsion.

The invention recognizes that an effective cosmetic formulation of an oil in water emulsion containing PHEMA should be based on a combination of relationships. Important relationships in such a formulation are those between the amount of PHEMA in the emulsion, the amount of plasticizer (a factor tied to the solvency power of the plasticizer in dissolving PHEMA) to the amount of PHEMA, and the effectiveness of the emulsifying agent to couple the components of the emulsion such that effective properties are imparted to the emulsion for the film forming of cosmetically useful PHEMA. This invention emphasizes the special relationship of the selection of emulsifying agent to the ultimate properties of the PHEMA film derived from the emulsion.

DETAILS OF THE INVENTION

PHEMA, which has been recommended for use as a component of a cosmetic formulation, is normally a brittle plastic which is insoluble in water. It is characterized as being hydrophylic; meaning that it has a strong affinity for water. The polymer is hygroscopic enough to attract and hold moisture. Indeed, PHEMA swells in contact with water, therefore a film of PHEMA on an epidermal surface can be swelled by the moisture present on the surface. PHEMA is readily soluble in alcohols such as methanol and ethanol, and can be dissolve in a solution of these alcohols and water up to about 80 weight percent water in the solution. These attributes have led to recommending PHEMA for use as a hair lacquer. The conversion of PHEMA into a flexible and pliable film without introducing a copolymeric component into its structure requires its plasticization with another material with which it is compatible. If the plasticizer is water soluble, it can be leached from admixture with PHEMA leaving behind the brittle polymer. In and case, plasticization with a most desirable plasticizer material in terms of permanence can result in a gummy film forming material.

It has been determined that PHEMA can be emulsified and plasticized but unless done so properly it cannot be made into an emulsion from which a water resistant, non-gummy and/or rubout-free film can be effected on an epidermal surface. It has been determined that PHEMA can be plasticized with a combination of water soluble and/or water dispersible plasticizers to effect a plasticized film possessed of a unique permanence in the presence of large amounts of moisture. The invention embraces the generation of a thin film of multi-plasticized PHEMA, e.e., a thin homogeneous film comprising a uniform dispersion of PHEMA and at least two different plasticizers for PHEMA, each having a different solvency power for PHEMA. The invention also includes the deposition of PHEMA from the aqueous phase of an oil in water emulsion in concert with (or cojointly with) the deposition of the oil phase thereof to form a thin film in which the oil phase and the PHEMA are sufficiently compatible to allow the components of the oil phase and the PHEMA to be essentially uniformly dispersed within the film as evidenced by the performance characteristics of the film. The invention also provides that in forming the film, the PHEMA is in solution with a solvent component which provides sufficient lipophilicity to assure such compatibility with the components of the oil phase.

It is an object of this invention to form PHEMA into a water resistant, non-gummy, hygroscopic, flexible and pliable thin layer when deposited on an epidermal surface.

It is another object of this invention to create a stable emulsion of a PHEMA in a cosmetic formulation, preferably a lotion formulation, from which a water resistant, non-gummy, hygroscopic, flexible and pliable thin layer of PHEMA can be formed when the cosmetic formulation is deposited on an epidermal surface.

It is a further object of this invention to create a process for the manufacture of a stable emulsion of a PHEMA which yields a water resistant, non-gummy, hygroscopic, flexible and pliable thin layer of the PHEMA when the emulsion is deposited on an epidermal surface.

Other objects of the invention are set forth herein.

PHEMA used in the practice of this invention, comprises an essentially linear[3] thermoplastic macromolecular structure of the recurring units of formula (I) above, especially PHEMA in which X of formula (I) is hydrogen. Preferably, such PHEMA has an weight average molecular weight of at least about 50,000, more desirably at least 100,000. Very desirable results have been obtained with the use of PHEMA having a weight average molecular weight of at least 200,000. As Abrahams, supra, points out, PHEMA is polymerizable to weight average molecular weights of 1,000,000 and more. Such PHEMA is usable for the practice of this invention, though PHEMA having a weight average molecular weight between about 100,000 and about 1,000,000 is more desirable for the practice of the invention. Most desirable results have been achieved using PHEMA having a weight average molecular weight of from about 200,000 to about 400,000.

[3]. "Essentially linear" means the PHEMA is sufficiently linear to be totally soluble in a 50-50 weight mixture of ethanol and water and have a $T_g$ of 105° C.

As pointed out above, it has been desired in the art to effect the plasticization of PHEMA so that when deposited as a film on any surface, it is more flexible than the unplasticized PHEMA. However, prior to this invention there has been an inadequate description in the art of the manufacture of an effective cosmetic formulation containing PHEMA as a film forming component which on application to an epidermal surface results in a pliant film which essentially replicates the pliancy of the epidermal surface. Heretofore, there has been a desire to introduce PHEMA to a water-based cosmetic formulation, but there has been a paucity of information leading to the manufacture of a stable water-based cosmetic emulsion of the oil in water variety.

There is described hereinafter a method by which the PHEMA can be made as a component of a stable oil in water emulsion which can be used as a cosmetic to provide an appropriately flexible and pliable (or pliant) film on skin. The invention effects the plasticization of PHEMA beyond simply making it into a more flexible material, because a modest improvement in flexibility is an insufficient alteration of the basic properties of PHEMA to allow its effective use for the generation of a lotion treatment of the skin which leaves a thin comfortable layer of water impermeable PHEMA on the skin. Comfort is effected by building into the PHEMA a high degree of pliability (or pliancy) so that when the film containing PHEMA is formed on the skin, the film conforms to the contortions and convolutions to which the pliable skin surface is put. In essence, the PHEMA film should have a level of pliability essentially equivalent to that of the skin to which it is applies. This invention achieve that as characterized by the formation of PHEMA into an effective stable oil in water emulsion possessed of the ability to deposit the film from a stable liquid phase,
the ability to deposit a uniform placticized film on the surface of the skin characterized by
good tactility and the pliancy of skin to provide a velvety smooth skin feel,
a freedom from greasiness and oiliness;
ready penetrability into the skin pores,
water resistant, non-gummy rubout characteristics,
non-adhesive bonding to hair so as to avoid conforming hair to a particular shape, and
moisture resistance combined with air and moisture permeability (breathability).

The formation of the thin PHEMA film of the invention on an epidermal surface is not easily determined. Because the film is deposited from a cosmetic formulation, there is also deposited with it cosmetic agents such as oils, surface active agents, moisturizers, and the like. The nature of the film can only be determined from the properties provided to the epidermal surface to which it is supplied. Such facts that after treatment the treated skin has less evaporative loss of moisture (perspiration) with moisture buildup on the skin and a longer lasting lotion effect than could be provided by the other ingredients of the cosmetic supports the belief that the PHEMA is present as a film on the skin. The extra moisture retained on the skin serves to moisten it, and this is a way of softening and smoothing out the skin.

On the basis of these attributes and the recognition of normal film forming properties of PHEMA, it is accepted that the PHEMA resides as part of a continuous film which resists moisture penetration because of the presence of PHEMA in the film and that PHEMA is essentially uniformly distributed in the film.

As pointed out above, there are many materials which can be used to plasticize PHEMA. It has been determined that when PHEMA is properly incorporated in a cosmetic formulation and properly combined with the plasticizer, the soft pliable PHEMA required for a cosmetic application, such as a cosmetic lotion, is achievable, otherwise it is not.

The plasticization of PHEMA starts with the selection of an active and volatile solvent for the PHEMA, followed by the use of progressively less active and progressively less volatile solvents for PHEMA. The solvation of PHEMA is the start of its plasticization. An aggressive solvent for PHEMA could dissolve the PHEMA and render it as part of a liquid solution. Such a material would be used in minimal amounts if the PHEMA is intended to be kept as a solid film. However, if the solvent is volatile, then it can be used in larger quantities in combination with a less volatile, or an essentially nonvolatile, solvent for PHEMA. Consequently, as the more volatile solvent is evaporated from the film of the deposited cosmetic emulsion, in which the PHEMA is held liquid by the presence of the more volatile solvent, a solid deposition of PHEMA occurs which is plasticized by the less volatile solvent present. When the less volatile solvent is more readily dissolved by water than one desires, then the presence of another still less volatile solvent can present in the formulation of PHEMA into the water phase of the emulsion which is less prone to ready solubilization by water. The treatment of PHEMA to make it an effective film forming material for cosmetic formulations, resides in its solvation for making the emulsion. The invention employs as the plasticization components a combination of solvents, ranging from active solvents which are volatile to less active solvents which are less volatile, indeed, by the standards of the invention, they may be termed nonvolatile.[4]

[4]. The terms "volatile" and "nonvolatile" are recognized as relative terms. Therefore, for convenience, a volatile solvent is one which evaporates from a 10 mil film within 24 hours of its deposition as a liquid onto an epidermal surface containing normal moisture, under an ambient temperature of 23° C. and normal pressure conditions. A nonvolatile solvent is one which will not evaporate entirely under those conditions.

The selection of solvents generally for making the water phase containing PHEMA is discussed elsewhere herein. However, it is suffice to say at this portion of the description that the plasticizers are solvents for PHEMA though in many instances, they may be such weak solvents that they require a cosolvent for effectiveness. Broadly speaking, the desirable nonvolatile plasticizers are aliphatic polyols, low molecular weight aliphatic polyethers and nonionic surface active agents (surfactant). The aliphatic polyols are normally liquid glycols and glycol ethers such as 1,2-propylene glycol, 1,3-propylene glycol, glycerine, diglyme, triglyme, tetraglyme, the monoalkyl ethers of them , such as the Carbitols and other methyl and ethyl endblocking ethers, and the like. The non-endblocked ethers may be reacted with ethylene oxide to form higher molecular weight compounds, to the extent the polymer is still liquid and not waxy. Other useful polyols include sorbitol, 1,2-butylene glycol, 1,2-hexylene glycol, glucose, fructose, sucrose, PEG-8, PEG-4, dipropylene glycol and honey.

The nonionic surface active agents (surfactants) contain molecular portions which are lipophilic (hydrophobic) and other molecular portions which are lipophobic (hydrophylic). These portions become the basis of determining their surface active properties by their hydrophilic-lipophilic balance (HLB). See Griffin, W. C. Emulsifier Evaluation By Water Absorption, Proc. of Scientific Section of Toilet Good Association, Vol. 6, pages 43–50 (Dec. 5, 1946 (cf. C.A. 41, p. 1133H). In the practice of this invention, if their HLB is low (e.g., about 2 or lower), their effectiveness in plasticizing the PHEMA effectively is poor. When their HLB is medium (e.g., about 4 to about 8), their effectiveness in plasticizing the PHEMA is better, but still weaker than desired for a commercial cosmetic formulation. However, nonionic surface active agents which have a high HLB (e.g., above about 8 and greater, typically not greater than 15) have been found to be superior plasticizing agents for PHEMA in the practice of the invention.

Desirable nonionics suitable for use as nonvolatile (solvents) plasticizers are the organic aliphatic ether compounds. They contain at least one ether group, generally at least three ether groups in the portion of the molecule which provides the lipophobic (hydrophylic) character to the surface active agent. The ether groups are desirably derived by the alkoxylation of an active hydrogen compound which provides the lipophilic (hydrophobic) character or property to the surface active agent. Preferred alkoxylated compounds are those derived from ethylene oxide and/or propylene oxide. Superior alkoxylated compounds are those derived from the alkoxylation of alcohols (aliphatic and aromatic) with ethylene oxide alone or a combination of ethylene oxide and 1,2-propylene oxide which provide a high HLB. It is most preferred that the lipophilic (hydrophobic) portion of the the nonionic surfactant molecule contain an aliphatic moiety containing at least 6

—CH$_2$— in sequence to form at least a hexylene bridge in the structure.

The preferred active hydrogen compounds for forming these plasticizers are the fatty alcohols containing at least about 8 carbon atoms and generally not greater than about 24 carbon atoms. The fatty alcohols are the hydrogenated versions of the fatty acid, though they may be synthesized by other synthetic routes, such as by the carbonylation of alkenes followed by hydrogenation of the oxo compound or the hydration of such alkenes.

Other nonionic surfactants which may be used differ in the nature of the lipophilic portion of the molecule. The choice of such portion is not narrowly critical so long as the surfactant has at least a medium, preferably a high, HLB. Thus, the lipophilic portion may be aralkyl, alkaryl, and the like.

The cosmetic formulation of the invention allows the inclusion of a variety of moisturizers/emollients other than the alcohols and surfactants characterized above, such as, e.g.:

hydrocarbons such as mineral oil, squalane, petrolatum, squalene, microcrystalline wax, paraffin, and the like;

lanolin and derivatives, such as lanolin alcohols, lanolin oil, lanolin, acetylated lanolin alcohols, acetylated lanolin, hydrogenated lanolin, hydroxylated lanolin, isopropyl lanolate, and the like;

silicones such as dimethicone, cyclomethicone, dimethicone copolyol, phenyl dimethicone, steroxy dimethicone, and the like;

fatty acids such as stearic acid, isostearic acid, myristic acid, linoleic acid, recinoleic acid, and the like;

fatty alcohols such as cetyl alcohol, stearyl alcohol, cetearyl alcohol, mytristyl alcohol, isostearyl alcohol, octyl dodecanol, and the like;

fatty acid esters such as isopropyl myristate, isopropyl palmitate, octyl palmitate, spermacell, isodecyl oleate, propylene glycol dicaprylate/dicaprate, glucose glutamate, isodecyl neopentanoate, isostearyl neopentanoate, myristyl myristate, jojoba oil, cetyl palmitate, octyl hydroxystearate, sorbitan trioleate, octyl stearate, dioctyl adipate, arachidyl propionate, isocetyl stearate, propylene glycol dipelargonate, myristyl lactate, C$_{12-15}$ alcohols benzoate, myreth-3 myristate, cetearyl octanoate, octadodecyl stearoyl stearate, glyceryl dilaurate, propylene carbonate, PPG-2 myristyl ether propionate, diisopropyl sebacate, octyl palmitate, neopentyl glycol dicaprate, disopropyl dimerate, cetyl lactate, decyl isostearate, butyl stearate, propylene glycol isostearate, isopropyl isostearate, and the like;

triglycerides such as sesame oil, sweet almond oil, avocado oil, hydrogenated soy bean oil, wheat germ oil, caprylic/capric triglycerides, apricot kernal oil, safflower oil, palm oil, grape seed oil, coconut oil, mink oil, peach kernal oil, shea butter, turtle oil, sunflower oil, hydrogenated vegetable oil, olive oil, rice bran oil, castor oil, corn oil cocoa butter, hydrogenated coconut oil, glyceryl trioctanoate, cherry pit oil, linseed oil, soy bean oil, and the like;

amino acids and polypeplides such as hydrolyzed animal protein, soluble collagen, collagen, milk protein, collagen amino acids, hydrolyzed elastin, elastin, elastin collagen complex, serine, glycine, proline, leucine, tyrasine, tryptophane, aspartic acid, valine, alanine, isoleucine, glutamic acid, soy protein, keratin amino acids, and the like;

other additives such as urea, lecithin, aloe vera, mucopolysaccharides (or hydrolyzed), soy sterols, cholesterol, lactic acid or salts, PCA and salts, PPG-10 cetyl ether, PPG-11 stearyl ether, polyamino sugar condensate, egg oil, PPG-3 myristyl ether, and the like.

Significant to the invention is the development of an emulsion system, involving the composition and process, which allows the provision of PHEMA as a stable cosmetically acceptable emulsion.

As a result, the compositions of the invention provide, in the deposition of the PHEMA containing film, for the presence of inter alias emulsifying agents. Illustrative of typical emulsifying agents are soaps such as ammonium, potassium and sodium stearates, ammonium, potassium and sodium palmitates, ammonium, potassium and sodium myristates, ammonium, potassium and sodium laurates, ammonium, potassium and sodium isostearates, ammonium, potassium and sodium oleates, aluminum stearate, magnesium stearate, beeswax/borax, lanolin acid soaps, and the like;

esters such as glyceryl stearate, sorbitan stearate, polysorbate 80, polysorbate 65, polysorbate 60, polysorbate 40, polysorbate 20, glycol stearate, PEG-2 stearate, PEG-10 stearate, PEG-30 stearate, PEG-40 stearate, PEG-100 stearate, PEG-150 stearate, PEG 1000 stearate, sorbitan palmitate, propylene glycol stearate, PEG-25 propylene glycol stearate, hydrogenated soy glyceride, wheat germ glyceride, palm oil glyceride, glyceryl oleate, glyceryl laurate, sorbitan oleate, PEG-12 distearate, polyglyceryl-10-decaoleate, PEG-8 oleate, methyl gluceth-20 sesquistearate, methyl glucose sesquistearate; and the like;

fatty alcohols such as cetyl alcohol, stearyl alcohol, cetearyl alcohol, and the like;

water soluble polymers such as Carbomer TM 934 (and salts), Carbomer TM 940 (and salts), Carbomer TM 941 (and salts), xanthan gum, cellulose gum, polyvinylpyrrolidone, carrogeenan, hydroxyethyl cellulose, gelatin, polyacrylamide, hydroxypropyl methyl cellulose, and the like;

sterols such as lanolin alcohol, cholesterol, soya sterol, hydrogenated lanolin, lanosterol, hydroxylated lanolin, and the like; ethers such as steareth-2, steareth-20, ceteareth-5, ceteareth-20, isosteareth-20, celeth-10, laureth-3, laureth-4, laureth-23, coceth-6, oleth-10, oleth-20, octyldodeceth-20, coleth-24, dihydrocoleth-15, PEG-10 soya sterols, PEG-25 soya sterols, methyl gluceth-20, PEG-5 soya sterol, PEG 5 pentaerythritol, PEG-40 castor oil, PPG-3 myristyl ether, PPG-15 stearyl ether; and the like;

anionic surfactants such as sodium lauryl sulfate, triethanolammonium lauryl sulfate, diethanolammonium lauryl sulfate, sodium cetyl sulfate, dioctyl sodium sulfosuccinate, disodium monococoamide sulfosuccinate, sodium isostearyl-2-lactylate, sodium cetearyl sulfate, sodium cocoyl isethionate, and the like;

amphoteric surfactants such as oleyl betaine, sodium laurimino dipropionate, sodium C$_{12-15}$ alkoxy propylimino dipropionate, and the like;

cationic surfactants such as stearamido diethylamine phosphate, cetrimonium bromide, stearalkonium chloride, PEG-15 cocamine; and the like; and as well, lecithin, magnesium aluminum silicate, microcrystalline wax, kaolin, ozokertte, ceresine, lauramide DEA, stearamide DEA, quaternium-18 hectorite, sodium caseinate, gelatin.

A number of the emulsifying agent provide moisturizing and/or emollience, as noted previously. A dual functionality for a number of the additives is recognized for the invention. As will be emphasized below, there are certain emulsifying agents which yield preferential results.

The invention contemplates the inclusion of a variety of other additives provided for the purpose of introducing special properties. It is not unusual in the practice of the invention to include such typical additives as preservatives, antioxidants, stabilizers, U.V. absorbers, vitamins and precursors, skin protectants, hormones, plant extracts, essential fatty acids, and the like. Illustrative of such further ingredients arein the category of preservatives, one may use methyl paraben, propyl paraben, quaternium-15, imidazolidinyl urea, butyl paraben, dehydroacetic acid (or salts), sorbic acid, sodium pyrithione, ethyl paraben, benzoic acid (or salts), formaldehyde, DMDM hydantoin, benzyl paraben, triclosan, glutaral, chlorhexidine digluconate, methylisothiazolinone, 2-bromonitropropane-1.3-diol, o-cymene-5-ol, and the like;

in the category of antioxidants and stabilizers, one may use BHA, tocopherol (or acetate), BHT, ascorbic acid (or palmitate), EDTA (and salts), propyl gallate, benzophenone-2, benzophenone-4, dilauryl thio diproprionate, and the like;

in the category of U.V. absorbers, one may use octyl dimethyl PABA, PABA, urocanic acid, benzophenone-2, benzophenone-5, benzophenone-9, ethyl dihydroxy PABA, and the like;

in the category of vitamins and precursors to vitamins, one may use retinal (or palmitate) (vitamin A), tocopherol (or acetate) (vitamin E), allantain calcium pantothenate, panthenol (vitamin B precursor), erocalciferol (vitamin D), panthenyl ethyl ether, and the like;

in the category of skin protectants, one may use dimethicone, allantain, and the like;

in the category of hormones, one may use pregnenolone succinate, and the like;

in the category of plant extracts one may use chamomile, rosemary, thyme, calendula oil, arnica oil, hayflower extract, cucumber extract, Lienis extract, matricaria oil, carrot extract, gentian extract, balm mint extract, juniper extract, pine needle extract, horse tail extract, red poppy extract, and the like;

in the category of essential fatty acids, one may use linoleic acid other miscellaneous ingredients for the cosmetic compositions of the invention include ribonucleic acid (and salts), oat flour, methyl nicotinate, hexyl nicotinate, royal bee jelly, allantoin acetyl methionine, cell extracts, mineral salts, polyamino sugar condensate, benzyl alcohol, aluminum chlorhydrate, salicylic acid, deproteinated yeast, allantoin polygalacturonic acid, adenosine disodium triphosphate, almond meal, oat meal rye flour, corn meal, egg powder, walnut shell powder, apricot seeds (crushed), and the like.

The above ingredients are provided in the cosmetic emulsions in accordance with standard practices. For example, the U.V. absorbers may be added to the cosmetic formulation in amounts ranging up to about 20 weight percent of the weight of the total formulation weight, though in the typical case the amount will not exceed about 12 weight percent, same basis, preferably not exceed about 10 weight percent. The U.V. absorber will be provided in the oil phase of the oil in water emulsion of the invention.

The cosmetic oil in water emulsion of the invention typically contains from about 50 to about 90 weight percent water, preferably 65 to 80 weight percent water, based on the total formulation weight of the emulsion. A feature of the cosmetic oil in water emulsion of the invention requires that it be stable for a minimum period of at least 2 years.

The stable oil in water emulsions of the invention contains from about 0.05 to about 2.0 weight percent of PHEMA, based on the total weight of the emulsion. In the preferred embodiment of the invention, the amount of PHEMA in the emulsion is about 0.1 to about 1.5, more preferably, about 0.3 to about 1.3 weight percent, same basis.

The ingredients of the stable oil in water emulsions of the invention, apart from the PHEMA, comprise the oils, humectins (moisturizing agents) and the emulsifying agents. These materials plus the PHEMA constitute important ingredients when the cosmetic oil in water emulsion is for use as a skin lotion. Because PHEMA is difficult to solubilize in a reasonably useful oil phase for cosmetic application, and is soluble in water, it is solvated for ready incorporation into the formulation.

The oil phase will typically comprise at least about 5 weight % of the weight of the emulsion, preferably from about 7 to about 15 weight % of the weight of the emulsion. The remainder is the water phase.

As pointed out above, solvation of PHEMA is the start of its plasticization. Solvation of the PHEMA is the start of its incorporation into the emulsion formulation. Plasticization of the PHEMA is related to the film forming and film performance characteristics of PHEMA. The following discussion relates to the solvation of PHEMA for making the emulsion of the invention.

Useful solvents for PHEMA are organic liquids employed alone or in combination with water. The solvents may range from those which are water soluble to those which are water dispersible. Many of the solvents are not effective alone as solvents but are effective solvents when used as part of a solvent combination in which a stronger solvent for PHEMA is used as part of the solvent combination. In that situation, one may term the stronger cosolvent as a common solvent for PHEMA and the weaker solvent.

The more active solvents are water soluble. The most effective active solvents, and which are typically the more volatile solvents are the lower alkanols containing 2 to 4 carbon atoms, such as ethanol, n-propanol, isopropanol, n-propanol, n-butanol, sec.-butanol and isobutanol. Though methanol is an effective solvent, it is to be avoided for toxicological reasons. Small amounts of these alkanols will plasticize PHEMA but because of their volatility, they are not used as permanent plasticizers. As a rule they are selected as the volatile solvent compound in combining PHEMA into the emulsion formulation.

PHEMA is known to be soluble in lower alkanol-water mixtures. For example, PHEMA may be dissolved in a water-ethanol mixture up to $\simeq$80/20 weight mixture of water (80%) and ethanol (20%). Lesser amounts of water may be employed to advantage. In this aspect of the invention, one may term the alkanol as coupling the water and the PHEMA.

Other useful solvents which are useful as plasticizers include the aliphatic polyols such as the normally liquid glycols and glycol ethers, e.g., 1,2-propylene glycol, 1,3-propylene glycol, glycerine, diglyme, triglyme, tetraglyme, the monoalkyl ethers of them, such as the Carbitols ™ and other methyl and ethyl endblocking ethers, and the like. The non-endblocked ethers may be reacted with ethylene oxide to form higher molecular weight compounds, to the extent the polymer is still liquid and not waxy. The preferred polyol is 1,2-propylene glycol. These solvents are effective plasticizers for PHEMA not only in solubilizing PHEMA but also in aiding in the ultimate plasticization of the PHEMA film deposited of the epidermal surface. They are nonvolatile solvents/plasticizers. They are all lower alkanol soluble, and therefore, one may use the lower alkanol to couple their solubility or rate of solution in water and PHEMA as well. Since the polyols and polyethers have greater solubility in water than PHEMA, they too may be used to enhance the solubility of PHEMA in water.

The preference for 1,2-propylene glycol stems from its high solvency power for PHEMA, its relative low volatility, its significant hygroscopicity and its favorable toxicological properties.

Therefore, combinations of the lower alkanols and the polyols may also be used to advantage. In fact, in the preferred formulation of the PHEMA into the emulsion, the solvent/plasticizer components are used to enhance the solubility of the PHEMA in the aqueous phase through the coupling effect achieved the lower alkanols, the polyol or ether components of the solvent system.

The last category of solvent/plasticizer are the nonionic surface active agents (surfactants) which contain both molecular lipophilic (hydrophobic) portions and molecular lipophobic (hydrophylic) portions. As pointed out above, these portions become the basis of determining their surface active properties by their hydrophilic-lipophilic balance (HLB).

In the practice of this invention, if their HLB is low (e.g., about 2 or lower), their effectiveness in plasticizing the PHEMA effectively is poor. When their HLB is medium (e.g., about 4 to about 8), their effectiveness in plasticizing the PHEMA is better, but still weaker than desired for a commercial cosmetic formulation. However, nonionic surface active agents which have a high HLB (e.g., above 8 and greater, typically not greater than 15) have been found to be superior plasticizing agents for PHEMA in the practice of the invention.

The nonionics are the weakest of the solvents for PHEMA. As a rule, they are used jointly with another more active solvent, such as the lower alkanols and the polyols/polyethers. Though they may be the weakest solvent, they serve a plurality of functions: as a rule, they are the least volatile of the solvent/plasticizers, and they function to compatibilize the deposited oil phase and the deposited PHEMA in the film.

Desirable nonionics suitable for use as nonvolatile solvents/plasticizers are the organic aliphatic ether compounds. They contain at least one ether group, generally at least three ether groups in the portion of the molecule which provides the lipophobic (hydrophylic) character to the surface active agent. The ether groups are desirably derived by the alkoxylation of an active hydrogen compound which provides the lipophilic (hydrophobic) character or property to the surface active agent. Preferred alkoxylated compounds are those derived from ethylene oxide and/or propylene oxide. Superior alkoxylated compounds are those derived from the alkoxylation of alcohols (aliphatic and aromatic) with ethylene oxide alone or a combination of ethylene oxide and 1,2-propylene oxide which provide a high HLB. It is most preferred that the lipophilic (hydrophobic) portion of the the nonionic surfactant molecule contain an aliphatic moiety containing at least 6 —$CH_2$— in sequence to form at least a hexylene bridge in the structure.

The preferred active hydrogen compounds for forming these solvent/plasticizers are the fatty alcohols containing at least about 8 carbon atoms and generally not greater than about 24 carbon atoms. The fatty alcohols are the hydrogenated versions of the fatty acid, though they may be synthesized by other synthetic routes, such as by the carbonylation of alkenes followed by hydrogenation of the oxo compound or the hydration of such alkenes.

Other nonionic surfactants which may be used differ in the nature of the lipophilic portion of the molecule. The choice of such portion is not narrowly critical so long as the surfactant has at least a medium, preferably a high HLB. Thus, the lipophilic portion may be aralkyl, alkaryl, and the like.

As noted above, the cosmetic emulsion formulation of the invention is predominantly water. Water will comprise the continuous phase of the emulsion and the oil phase will comprise the discontinuous phase of the emulsion. The water phase is not water alone. It comprised the PHEMA and the solvent/plasticizers for PHEMA.

The cosmetic emulsion formulation of the invention is produced by the combination of multiple phases of the components, starting with one or more oil phases and including thereafter one or more aqueous phases. The various phases are separately produced and then combined to produce the desired emulsion. The combination of any phase with another phase is effected with stirring sufficient to effect the degree of admixture sought.

As a rule, the separately generated oil phase is frequently created by mixing the oil phase components thereof at an elevated temperature. The elevated temperature is required to cause normally solid materials to melt and to effect compatibility between materials which at lower temperatures have limited compatibility. Many times, the elevated temperature will exceed about 35° C. and, in the typical case, the elevated temperature will range from about 50° C. to about 100° C., though in most cases, it has been found that the elevated temperature ranges from about 60° C. to about 85° C. The so formed oil phase can then be mixed with water to form either a water in oil emulsion or a oil in water emulsion. Whichever type of emulsion that is formed is unimportant because the ultimate and finished emulsion will be an oil in water emulsion type even if an emulsion inversion of a water in oil emulsion is necessary at the end or last step of the procedure.

The PHEMA is typically provided in a water phase in combination with the solvent and at least a portion of the plasticizer. It has been preferred to combine the organic solvent and at least a portion of the plasticizer with the PHEMA with sufficient stirring to dissolve the PHEMA and form a solution. That mixture can be combined with sufficient stirring to more of the aqueous phase to form a solution.

A separate phase of the formulation, and a feature of the desired emulsification procedure, is to separately form an aqueous phase with the emulsifying agent for the whole emulsion formulation. The terminology of "separately form" means that the phase is separate from the oil phase and the aqueous phase containing the PHEMA. That separate phase containing the emulsifying agent may be initially combined with the oil phase to form either an oil in water emulsion or a water in oil emulsion as an intermediate emulsion. Thereafter, more of the water phase is combined with this intermediate emulsion to produce the final emulsion. The choice of emulsifying agent has proven very significant in the performance of the invention. It has been determined in the case of certain formulations that the choice of emulsifying agent can materially benefit the performance of the resulting cosmetic emulsion in terms of stability and performance.

Preferred emulsifying agents in the practice of the invention comprise anionic surfactants such as ammonium stearate, triethanolammonium stearate, sodium lauryl sulfate, triethanolammonium lauryl sulfate, diethanolammonium lauryl sulfate, sodium cetyl sulfate, dioctyl sodium sulfosuccinate, disodium monococoamide sulfosuccinate, sodium isostearyl-2-lactylate, sodium cetearyl sulfate, sodium cocoyl isethionate, and the like;

The preferred emulsifying agents are the ammonium salts of the long chain fatty acids, typically $C_{12+}$ in carbon length. The most favorable are ammonium salts of the long chain saturated fatty acids, $C_{12+}$, preferably $C_{16+}$, in length, such as ammonium stearate, formed by the in situ reaction of stearic acid (typically provided in the oil phase) and ammonium hydroxide (typically provided in an aqueous phase). In fact, ammonium stearate has proven to be a special case. It has proven to be an excellent emulsifying agent because it forms and maintains highly stable emulsions which are stable to heating of about 40° C. for over 6 months. Because of the high volatility associated with the release of ammonia when the emulsion is coated on skin, the surfactant qualities provided by ammonium stearate are sufficiently altered that the resulting cosmetic film on the skin possesses optimum film forming characteristics because of a rapid insolubilization of the PHEMA after it is laid down as a film. This contributes to the water impenetrability of the resultant coating making the film more retentive of the moisture on the skin surface and better at protecting the skin surface from foreign elements. Another feature is that the plasticizer in the film is less leachable by the effects of moisture. The use of ammonium hydroxide combined with stearic acid contributes to the production as well of a cosmetically elegant emulsion which is devoid of robust characteristics.

The amount of the solvent/plasticizer in the emulsion is not narrowly critical. Any amount which provides the benefits of the invention are usable. Typically, one will wish to employ at least about 3 times the weight of the volatile solvent/plasticizer to the weight of PHEMA in the emulsion of the invention. Normally, the amount of the volatile solvent/plasticizer employed will range from about 4 to about 15 times the weight of PHEMA in the emulsion. The lesser volatile solvents/plasticizer vary in concentration to the amount of PHEMA present in the emulsion based on the tactility effects sought for the cosmetic emulsion when applied to skin. For example, the polyol solvent/plasticizers may be present in an amount ranging from about 10 weight percent to about 20 times the weight of the PHEMA in the emulsion while the nonionic surfactant solvent/plasticizers may range from about 0.01 weight percent to about 10 times the weight of the PHEMA in the emulsion. These values can be adjusted below and above these values in order to achieve special cosmetic effects.

Experimental work has demonstrated the importance of the manner is which the oil in water emulsion is formed to the ability of PHEMA to form an effective stable emulsion suitable for cosmetic purposes. Table I below illustrates a typical prior art method for making a commercially acceptable cosmetic lotion product using, in these instances, PHEMA.

TABLE I

| Ingredient | 1 wt. % | 2 wt. % | 3 wt. % | 4 wt. % |
|---|---|---|---|---|
| Phase A | | | | |
| Glycerol Monostearate | 2.4 | 2.4 | 2.4 | 2.4 |
| Triple Pressed Stearic Acid | 2.0 | 2.0 | 2.0 | 2.0 |
| Palmitic Acid | 0.8 | 0.8 | 0.8 | 0.8 |
| Cetyl Alcohol | 1.2 | 1.2 | 1.2 | 1.2 |
| Lanolin | 0.4 | 0.4 | 0.4 | 0.4 |
| Propyl Paraben | 0.1 | 0.1 | 0.1 | 0.1 |
| PHEMA | — | — | 2.0 | — |
| 30% PHEMA/PG[5] | 3.5 | — | — | — |
| 20% PHEMA/PG[6] | — | 3.5 | — | — |
| 10% PHEMA/PG[7] | — | — | — | 3.5 |
| Phase B | | | | |
| 2% Carbopol ™/H$_2$O | 5.0 | 5.0 | 5.0 | 5.0 |
| Aloe Vera Gel | 20.0 | 20.0 | 20.0 | 20.0 |
| Methyl Paraben | 0.15 | 0.15 | 0.15 | 0.15 |
| Water | 53.85 | 53.85 | 51.85 | 52.45 |
| Glycerine | — | — | 3.5 | — |
| Phase C | | | | |
| 50% Sol Triethanolamine/H$_2$O[8] | 0.6 | 0.6 | 0.6 | 2.0 |
| Q.S. Water | 10.0 | 10.0 | 10.0 | 10.0 |
| | 100.0 | 100.0 | 100.0 | 100.0 |

5. 30/70 wt. mixture of PHEMA in 1,2-propylene glycol
6. 20/80 wt. mixture of PHEMA in 1,2-propylene glycol
7. 10/90 wt. mixture of PHEMA in 1,2-propylene glycol 8. 50% solution of TEA in water The processing of the phases was a three phase system for generating an emulsion using a typical addition of the water phases to oil phase emulsion. In each case, the Phase A's were heated to 71° C. to effect admixture of the components of the phase. The Phase B's are typical of the water phases used in cosmetic emulsions and contain a preservative, moisturizer and gelling agent. In each example, it was found that globules of PHEMA precipitated from the emulsions demonstrating emulsion instability.

As indicated above, the amount of PHEMA in the emulsion contributes to the performance of the ultimate cosmetic coating of PHEMA when deposited on skin. Table II below illustrates emulsion formulations with different levels of PHEMA solubilized in propylene glycol.

TABLE II

| Ingredient | 5 wt. % | 6 wt. % |
|---|---|---|
| Phase A | | |
| Glycerol Monostearate | 2.4 | 2.4 |
| Triple Pressed Stearic Acid | 2.0 | 2.0 |
| Palmitic Acid | 0.8 | 0.8 |
| Cetyl Alcohol | 1.2 | 1.2 |
| Lanolin | 0.48 | 0.48 |
| Propyl Paraben | 0.1 | 0.1 |
| Phase B | | |
| 2% Sol. Carbopol ™/H$_2$O | 5.0 | 5.0 |
| Glycerine | 3.5 | 3.5 |
| Methyl Paraben | 0.15 | 0.15 |
| Water | 43.57 | 43.57 |
| 10% PHEMA/PG | 30.0 | 15.0 |

TABLE II-continued

|  | Example No. | |
|---|---|---|
| Ingredient | 5 wt. % | 6 wt. % |
| Phase C | | |
| 50% Sol. Triethanolamine/H₂O | 0.5 | 0.5 |
| Phase D | | |
| Q.S. Water | 10.0 | 10.0 |
| Color | 0.2 | 0.2 |
| Fragrance | 0.1 | 0.1 |
|  | 100.0 | 100.0 |

The emulsions were made using the typical water phase added to oil phase emulsion procedure described above with respect to Examples 1–4. The products of Examples 5 and 6, at first blush, appeared to be commercially acceptable lotions but on closer inspection, they each showed the PHEMA to be suspended in the emulsions. Globules of PHEMA were present and when the emulsion formulations were rubbed out on skin, they each were gummy films which balled up on the skin surface.

As pointed out above, lower alkanols are effective solvents which serve to couple other plasticizers for PHEMA. Table III below records certain experiments demonstrating the use of a lower alkanol such a ethanol as a coupling agent for solubilizing PHEMA in an aqueous system and using propylene glycol as a cosolvent and a number of surfactants. PHEMA was used at 8 weight % based on findings from other solubility studies.

The experimental procedure used in Examples 7–11 set forth in Table III below involved the following steps:
1. Solubilize PHEMA in ethanol first, then add the 1,2-propylene glycol to form a homogeneous solution.
2. Dissolve the surfactant component in water.
3. Slowly added the solution from 2. to the solution from 1. under high shear.

TABLE III

|  | Example No. | | | | |
|---|---|---|---|---|---|
|  | 7 | 8 | 9 | 10 | 11 |
| Ingredient | Grams By Wt. | Grams By Wt. | Grams By Wt. | Grams By Wt. | Grams By Wt. |
| ETOH 95% | 7.5 | 7.5 | 7.5 | 7.5 | 7.5 |
| Propylene Glycol | 5.0 | 5.0 | 5.0 | 5.0 | 5.0 |
| PHEMA | 2.0 | 2.0 | 2.0 | 2.0 | 2.0 |
| Surfactant | | | | | |
| BRIJ 78[9] | 0.2 | — | — | — | — |
| Arlacel C.[10] | — | 0.2 | — | — | — |
| Atlas G-100[11] | — | — | 0.2 | — | — |
| Tween 80[12] | — | — | — | 0.2 | — |
| Span 60[13] | — | — | — | — | 0.2 |
| Water | 10.0 | 10.0 | 10.0 | 10.0 | 10.0 |
| Comments: | Clear Sol'n no rubout on skin | Globules on stirrer | No globules sl. oily rubout on skin | Looks clear sl. foamy sl. rubout on skin | Globules on stirrer |

[9]20 moles ethylene oxide ethoxylate of stearyl alcohol.
[10]Sorbitan sesquioleate.
[11]Dimethyl isosorbite.
[12]20 moles ethylene oxide ethoxylate of sorbitan oleate.
[13]Sorbitan monostearate.

It was found that the solvent/plasticizers had to be added to water or desired clear solutions did not result. Stables emulsions would not be obtainable in the absence of ethanol and 1,2-propylene glycol from the above formulation.

Table IV illustrate the formulation of a cosmetic lotion formulation by the provision of the PHEMA solvents from a common water phase, in this instance, as phase C.

TABLE IV

|  | Example No. |
|---|---|
|  | 12 |
| Ingredient | wt. % |
| Phase A | |
| Glycerol monostearate | 2.4 |
| Triple pressed stearic acid | 2.0 |
| Cetyl alcohol | 1.2 |
| Palmitic acid | 0.8 |
| Lanolin | 0.48 |
| Propyl Paraben | 0.1 |
| Phase B1 | |
| Methyl Paraben | 0.15 |
| Water | 58.07 |
| Phase B2 | |
| 50% Sol. Triethanolamine/H₂O | 0.5 |
| Phase C | |
| Propylene Glycol | 7.5 |
| ETOH | 5.0 |
| PHEMA | 1.5 |
| BRIJ 78 | 0.2 |
| Water | 9.9 |
| Phase D | |
| Q.S. Water | 10.0 |
| Color | 0.2 |
| Fragrance | 0.1 |
|  | 100.0% |

The formulation of Table IV was made into an emulsion by the following two processes:
1. Typical oil in water emulsion in which: Phase B1 was added to phase A. Then phase B2 was added to the combined phase A and phase B1 to bring to them to a proper pH of approximately 6.0. Afterwards, phases C and D were added in sequence. The oil phase was made at 71° C. and mixed with the other phases at that temperature using moderate shear mixing with a standard propeller blade mixer.
2. Typical oil in water emulsion in which: Phase B1 was added to phase A. Next, phase C was added to the combined phase A and phase B1. This solution was then brought to proper pH by the addition of phase B2. Phase D was then introduced. The oil phase was made at 71° C. and mixed with the other phases at that temperature using moderate shear mixing with a standard propeller blade mixer.

The results of these two procedures with the formulation of Example 12 were as follows:
A. Procedure 1 above yielded a borderline commercially acceptable product. Slight rubout of the PHEMA was obtained when the lotion was applied to skin. Experimental experience indicated that the rate of addition of phase C was too fast, suggesting that there was a correlation between performance and the rate at which emulsification was effected, i.e., the rate at which the oil and water phases were combined.
B. Procedure 2 above yielded a thin unacceptable product in which PHEMA globules were present. Experience suggested that a pH adjustment at end of the procedure was required to stabilize the PHEMA in the water phase.

Table V illustrates the modification of the formulation of Table V above by substituting triethanolamine with stearyl pyridinium chloride.

TABLE V

| Ingredient | Example No. 13 wt. % |
|---|---|
| Phase A | |
| Glycerol monostearate | 2.4 |
| Triple pressed stearic acid | 2.0 |
| Cetyl alcohol | 1.2 |
| Isopropyl myristate | 0.8 |
| Lanolin | 0.48 |
| Propyl Paraben | 0.15 |
| Phase B | |
| Methyl Paraben | 0.3 |
| Water | 58.87 |
| Stearyl pyridinium chloride | 1.0 |
| Phase C | |
| Propylene glycol | 7.5 |
| ETOH | 5.0 |
| PHEMA | 1.5 |
| BRIJ 78 | 0.2 |
| Water | 9.8 |
| Phase D | |
| Q.S. Water | 8.5 |
| Fragrance | 0.1 |
| Color | 0.2 |
| | 100.0% |

The procedure used for Example 13 was procedure 1 used for Example 12 except the stearyl pyridinium chloride was added as part of Phase B to create the emulsion. Several levels of stearyl pyridinium chloride were also investigated. The formulation of Example 13 was found to be too viscous. The emulsion was initially stable but separation occurred overnight.

As one might expect, there was found a performance relationship between the selection of emulsifying agent and the formulation in general. Table VI illustrates experiments with another emulsifier, sodium cetearyl sulfate, the incorporation of Silicone 200 (a polydimethylsiloxane) to improve cosmetic elegance, and the addition of glycerine to judge effects on humectant properties. These formulas had a reduced oil Phase (A) to decrease viscosity, and there was a decrease on the amount of PHEMA in the formulae of Examples 15 and 16.

TABLE VI

| | Example No. | | |
|---|---|---|---|
| Ingredient | 14 wt. % | 15 wt. % | 16 wt. % |
| Phase A | | | |
| Glycerol Monostearate | 1.5 | 1.5 | 1.5 |
| Triple pressed stearic acid | 1.0 | 1.0 | 1.0 |
| Cetyl alcohol | 1.0 | 1.25 | 1.25 |
| Isopropyl myristate | 1.0 | 0.5 | 0.5 |
| Lanolin | 0.5 | 0.5 | 0.5 |
| Propyl Paraben | 0.15 | 0.15 | 0.15 |
| Neobee M-5 | 0.7 | 0.3 | 0.3 |
| Silicone 200 | — | 0.5 | — |
| Glycerine | — | — | 0.5 |
| Phase B | | | |
| Methyl Paraben | 0.3 | 0.3 | 0.3 |
| Water | 60.88 | 50.0 | 50.0 |
| Sodium Cetearyl sulfate | 0.35 | 0.35 | 0.35 |
| Phase C | | | |
| Propylene Glycol | 7.5 | 7.5 | 7.5 |
| ETOH | 5.0 | 5.0 | 5.0 |
| PHEMA | 1.5 | 1.0 | 1.0 |
| BRIJ 78 | 0.02 | 0.02 | 0.02 |
| Water | 9.8 | 9.8 | 9.8 |
| Phase D | | | |
| Q.S. Water | 8.5 | 20.03 | 20.03 |
| Color | 0.2 | 0.2 | 0.2 |
| Fragrance | 0.1 | 0.1 | 0.1 |
| | 100.0% | 100.0% | 100.0% |

The procedure for making the emulsions of Examples 14–16 was the same as procedure 1 used with Table IV supra. In these Examples, phase C was added very slowly. Another study similar to Example 12 showed that the amount of BRIJ 78 could be reduced to 0.02 wt. % in the finished formulations; this helped in avoiding aeration during blending of the emulsion.

The formulation of Example 14 as made above produced a lotion which was viewed to be a commercially acceptable product. The lotion of Example 14 did not cause rubout of PHEMA on skin.

With respect to Example 15, the silicone proved to be incompatible with PHEMA causing at least a portion of the PHEMA to precipitate. Reformulation would be be required to allow incorporation of such a silicone into this type of lotion formulation.

With respect to Example 16, glycerine was not sufficiently compatible in the solvent system of the formulation and as a result, it was incompatible with the PHEMA causing at least a portion of the PHEMA to precipitate.

As pointed out above, ammonium stearate, formed by the in situ reaction of ammonium hydroxide and stearic acid, has proven to be a unique emulsifying agent. The volatility of the ammonium group aids in developing optimum PHEMA film forming capabilities while the salt provides excellent emulsion stabilization. The following Table VII comprises the formulations for Examples 17 and 18. The examples demonstrate the use of ammonium hydroxide and stearic acid as the emulsifying agent and the use of different levels of PHEMA.

TABLE VII

| | Example No. | |
|---|---|---|
| Ingredient | 17 wt. % | 18 wt. % |
| Phase A | | |
| Glycerol monostearate | 1.7 | 1.7 |
| Triple pressed stearic acid | 2.55 | 2.55 |
| Cetyl alcohol | 1.7 | 1.7 |
| Isopropyl palmitate | 0.42 | 0.42 |
| Lanolin | 0.42 | 0.42 |
| Propyl Paraben | 0.15 | 0.15 |
| Caprylic/Capric triglycerides | 0.25 | 0.25 |
| Phase B1 | | |
| Methyl Paraben | 0.3 | 0.3 |
| Water | 65.0 | 65.0 |
| Phase B2 | | |
| 20% Sol. Ammonium Hydroxide/$H_2O$ | 1.0 | 1.0 |
| Phase C1 | | |
| Water | 9.8 | 9.8 |
| BRIJ 78 | 0.02 | 0.02 |
| Phase C2 | | |
| Propylene Glycol | 7.5 | 7.5 |
| ETOH | 5.0 | 5.0 |
| PHEMA | 0.5 | 1.2 |
| Phase D | | |
| Q.S. Water | 3.39 | 2.69 |
| Color | 0.2 | 0.2 |
| Fragrance | 0.1 | 0.1 |
| | 100.0 | 100.0 |

The procedure employed in Examples 17 and 18 are as follows:
1. The ingredients of Phase A were weighed and put into a beaker suitable for heating to 160° F. (71° C.)
2. The ingredients of Phase B1 were weighed and put into a beaker suitable for heating to 160° F. (71° C.)
3. A 20 wt. % solution of ammonium hydroxide in water was separately prepared for Phase B2; it was not heated.
4. The ingredients of Phase C1 were weighed out and heated to 100° F. (38° C.)
5. The ingredients of Phase C2 were weighed out and mixed in a suitable container, as follows:
   a. The ethanol (ETOH) was added the 1,2-propylene glycol and the mixture was stirred.
   b. Feathered PHEMA into ETOH/propylene glycol solution under high shear on Lightnin' type mixer.
6. Phase C1 was slowly added to Phase C2 under high shear and the mixing was continued until the mixture was uniform. No heat was intentionally applied in this step.
7. Phases A and B1 were heated to 160° F. (71° C.); Phase B1 was then slowly added to Phase A and mixing was continued until uniform.
8. Phase B2 was added to the mixture of Phases A and B1 to form an emulsion. Mixing was continued until the emulsion appeared uniform.
9. The combined Phase C was heated to 100° F. (38° C.)
10. When the emulsion is formed from the combination of Phase B2 and the mixture of Phases A and B1, combined Phase C was added with moderate stirring to the emulsion at a flow rate of no more than 6 milliliters per minute per 1000 milliliters of finished product.
11. When Phase C addition was complete, Phase D was added to the emulsion.
12. Stirring was continued until the emulsion reached room temperature (ambient, about 23° C.).
13. The finished emulsion had a pH ranging between 5.8 and 6.4

Example 17 contained 0.5 wt. % of PHEMA. The emulsion of Example 17 was cosmetically elegant emulsion, exhibiting no rubout or gummy characteristics when applied as a lotion to skin. Accelerated storage studies showed this emulsion to hold its characteristics at a temperature of 100° F. (38° C.) for over 6 months.

Example 18 contained 1.2 wt. % of PHEMA. The emulsion produced a cosmetically acceptable lotion. However, the lotion (emulsion) exhibited a slight rubout characteristic on application to skin. At accelerated storage conditions at 40° C. for 2–3 months, some of the PHEMA precipitated.

We claim:

1. A stable oil in water emulsion containing an ammonium salt of a long chain fatty acid as a emulsifying agent, 2-hydroxyethyl methacrylate homopolymer in the aqueous phase and a combination of 2-hydroxyethyl methacrylate homopolymer solvents of different activities, at least one is volatile and at least one is nonvolatile, in said aqueous phase.

2. A composition of matter comprising a thin film from the topical application of a stable emulsion of the oil and water emulsion of claim 1 from which a water resistant, non-gummy, hygroscopic, flexible and pliable thin film of 2-hydroxyethyl methacrylate homopolymer is deposited on an epidermal surface.

3. A cosmetic formulation comprising the emulsion of claim 1.

4. A composition of matter comprising a thin film from the cosmetic topical application of a stable emulsion of the oil and water emulsion of claim 1 from which a water resistant, non-gummy, hygroscopic, flexible and pliable thin film of 2-hydroxyethyl methacrylate homopolymer is deposited on an epidermal surface.

5. A cosmetic oil in water emulsion comprising the stable oil in water emulsion of claim 1 in which said emulsion contains an oil phase and a water phase which comprises 2-hydroxyethyl methacrylate homopolymer in the water phase, at least three solvents for 2-hydroxyethyl methacrylate homopolymer, and an ammonium salt of a long chain fatty acid as an emulsifying agent.

6. The emulsion of claim 5 wherein the solvents for 2-hydroxyethyl methacrylate homopolymer comprise
a. an active and volatile solvent,
b. a lesser intermediately active and nonvolatile solvent and
c. a least active and nonvolatile solvent.

7. The emulsion of claim 6 wherein the ammonium salt is ammonium stearate.

8. The emulsion of claim 6 wherein the solvents for 2-hydroxyethyl methacrylate homopolymer comprise
   i. ethanol as an active and volatile solvent,
   ii. 1,2-propylene glycol as a lesser intermediately active and nonvolatile solvent and
   iii. a nonionic surfactant as a least active and nonvolatile solvent.

9. The emulsion of claim 8 wherein the nonionic surfactant is an ethoxylate of a fatty alcohol.

* * * * *